(12) United States Patent
Stanley

(10) Patent No.: US 9,393,008 B2
(45) Date of Patent: Jul. 19, 2016

(54) SUTURE CLAMP

(75) Inventor: Cleon Stanley, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 683 days.

(21) Appl. No.: 13/568,606

(22) Filed: Aug. 7, 2012

(65) Prior Publication Data
US 2013/0079820 A1   Mar. 28, 2013

Related U.S. Application Data

(60) Provisional application No. 61/537,825, filed on Sep. 22, 2011.

(51) Int. Cl.
  *A61B 17/04*  (2006.01)
(52) U.S. Cl.
  CPC ...... *A61B 17/0401* (2013.01); *A61B 2017/0414* (2013.01); *A61B 2017/0446* (2013.01); *A61B 2017/0451* (2013.01); *A61B 2017/0459* (2013.01); *A61B 2017/0462* (2013.01)
(58) Field of Classification Search
  CPC ........... A61B 17/04; A61B 2017/0409; A61B 2017/0414; A61B 17/0487; F16G 11/00; F16G 11/04; F16G 11/041
  See application file for complete search history.

(56) References Cited

U.S. PATENT DOCUMENTS

| | | | |
|---|---|---|---|
| 4,022,218 A * | 5/1977 | Riddick | 604/266 |
| 4,291,698 A * | 9/1981 | Fuchs | A61B 17/0487 24/132 AA |
| 4,387,489 A | 6/1983 | Dudek | |
| 5,258,015 A | 11/1993 | Li et al. | |
| 5,474,572 A | 12/1995 | Hayhurst | |
| 5,645,553 A | 7/1997 | Kolesa et al. | |
| 5,919,208 A | 7/1999 | Valenti | |
| 6,074,409 A | 6/2000 | Goldfarb | |
| 6,231,592 B1 | 5/2001 | Bonutti et al. | |
| D465,843 S * | 11/2002 | Guala | D24/129 |
| 7,001,412 B2 | 2/2006 | Gallagher et al. | |
| 7,686,830 B2 | 3/2010 | Collier et al. | |
| 2005/0288711 A1* | 12/2005 | Fallin et al. | 606/232 |
| 2010/0256676 A1* | 10/2010 | Hay | A61B 17/0487 606/232 |

* cited by examiner

*Primary Examiner* — Katherine M Shi
*Assistant Examiner* — Michael Mendoza
(74) *Attorney, Agent, or Firm* — Woodard, Emhardt, Moriarty, McNett & Henry LLP (57) ABSTRACT

Among other things, there is disclosed embodiments of devices to hold sutures extending from the skin, such as suture portions of a suture anchor. Methods of using such devices are also disclosed.

15 Claims, 6 Drawing Sheets

SUTURE CLAMP

REFERENCE TO RELATED APPLICATION

This application claims the benefit of U.S. Provisional Application No. 61/537,825, filed Sep. 22, 2011, which is hereby incorporated by reference.

BACKGROUND

The present disclosure concerns devices and methods for holding sutures extending from the skin of a patient in tension. In particular, the disclosure provides for easy snapping of devices onto an extending suture with minimal preparation.

In a number of surgical situations, such as the closing of wounds and the maintenance of a suture anchor for access to the gastrointestinal system, it frequently is necessary to hold or clamp on the skin sutures or similar material under significant tension or stress. Such clamps may be needed for a relatively long period (e.g. up to several weeks or more) to accommodate healing, facilitation of access or other long-term conditions, and thus can present a substantial risk of pain or other irritation of the skin or adjacent tissues. In an example of maintaining a suture anchor in the body for gastrointestinal access, the suture is used to pull the stomach wall close to or against the peritoneal wall so that an access port can be inserted through the skin, peritoneum and stomach wall for direct access to the interior of the stomach. The suture extends out through the skin, and a clamp is used to ensure that the tension on the suture which holds the stomach close to or against the peritoneal wall is maintained.

In many types of surgical procedures, it is known to use a suture anchor to hold tissues together. For example, in the field of gastroenterology, suture anchors have been used in enterostomy procedures to hold a portion of a viscus (e.g. the stomach or other abdominal organ) in place against another tissue portion, such as the abdominal wall or another organ. In the case of a gastrostomy, for example, a suture has a sturdy elongated piece (e.g. a thin bar or similar anchor member) that is freely movable attached at or near one end of the suture. A needle is inserted through the abdominal wall and stomach wall, and the elongated piece with the trailing suture is inserted through the needle and into the stomach. The elongated piece is longer than the width of the needle and the hole through the tissue, and so it is unable to be pulled back through the needle or hole unless it is exactly positioned along the hole or needle.

The suture extending through the tissues (and perhaps within the needle) is pulled. The pulling force is transmitted to the elongated piece, which is forced against the interior of the stomach, and pulls a portion of the stomach toward the abdominal wall. Procedures and existing suture anchors are exemplified in U.S. Pat. No. 6,699,263 to Cope, owned by the assignee of the present application and incorporated herein by reference in its entirety. The stomach tissue is pulled against the abdominal wall for ease of insertion of other devices, such as catheters for drainage or administration of therapy. The drawing together creates a seal between the abdominal wall and stomach tissues so as to help prevent fluid traffic between the stomach and abdominal cavity, which may result in peritonitis or other infections or complications involving the stomach or abdominal tissues. In some cases, the suture anchor remains in place for a period of days or weeks so as to ensure a desired engagement and stability between tissues.

One method known to keep the tension on the suture so as to maintain the tissues against each other—the stomach against the abdominal wall in the above example—uses a hemostat or other clamping device to crimp one or more metal crimp beads to the suture outside the patient. Having pulled the stomach toward and against the abdominal wall, the stomach tends to pull back on the elongated piece and suture. The crimped bead(s) hold the suture, ideally preventing it slipping through the hole in the tissue, and in the process the bead(s) are pulled against the patient's skin. While effective, this procedure has certain drawbacks. Patient discomfort and the close work of crimping the bead(s) are among such drawbacks. The size of and potential for pinching or sharp edges can injure or irritate surrounding tissue or enlarge the hole. The pull on the suture forces the bead(s) against the skin, resulting in poking discomfort from a small-surface-area item being pressed against the skin. There is a risk of slippage of the suture within the bead(s), especially if the crimp is initially insufficient. There is also the risk of cutting the suture inadvertently during crimping. Metals used for the bead(s) are generally incompatible with MRI procedures for reviewing the status of the procedure. The small size of the bead(s) and the necessity of accurate placement to ensure maintaining tension without injuring the patient makes for difficult and close work for the surgeon.

Another standard method for maintaining the tissues together is to anchor the free end of the suture in the patient's skin, as by sewing the suture into the skin directly. With at least local anesthetic from the insertion of the suture anchor, additional piercings of the skin to hold the free end of the suture may cause minimal initial discomfort, but discomfort will increase as the duration of the suture anchor in the body extends. With additional skin piercings to fasten the tensioned suture, there is also an increase in the potential for infection or other complications, and thus additional discomfort for the patient and work for the health-care provider, Accordingly, there remain needs for a suture anchor holding mechanisms that have less risk for discomfort to the patient, especially in cases where the suture anchor needs to remain in the patient for a substantial period of time, and which is easier are use than current techniques.

SUMMARY

Among other things, there is disclosed a suture clamp that has first and second portions with a hinge connection joining them. In exemplary embodiments, the first portion has an upper surface, a lower surface, at least one chamber between the upper and lower surfaces, and a suture channel, with the suture channel including a first opening through the upper surface and a second opening through the lower surface. The suture channel passes through the at least one chamber. The second portion has an upper surface, a lower surface, and at least one finger, each of the at least one finger being sized and configured to fit within a respective one of the at least one chamber. The portions are pivotable about the hinge connection between an open configuration in which the at least one finger is not within the at least one chamber and a closed configuration in which the at least one finger is at least partially within the at least one chamber so that the suture channel intersects the at least one finger. In such examples, when in the open configuration a suture extending through the suture channel can be linear as it passes through the at least one chamber, and in the closed configuration the suture is non-linear within the at least one chamber and contacts at least a portion of the at least one finger within the at least one chamber.

In some embodiments, a suture clamp can further include a lower disc part attached to the lower surface of at least one of the first and second portions. Such a lower disc part may be elastomeric and/or have a diameter larger than a diameter of the above-noted portions when in the closed configuration. A lower disc part may be monolithic with one of the portions. Further, a lower disc part could include one or more protrusions, and at least one of the portions may include one or more cavities for accommodating such protrusion(s), so that one or both of the first and second portions are assembled to the lower disc part by inserting the protrusion(s) into the cavity(s).

Examples of the first portion can include first and second chambers separated by a partition, with the partition forming a surface of the first chamber and a surface of the second chamber, and the suture channel can include an opening between the first and second chambers through the partition. A second portion can include first and second fingers sized and configured to snap fit within the first and second chambers, respectively. Such multiple chambers may be vertically stacked, e.g. a first chamber is located between the upper surface of the first portion and the second chamber, and the second chamber is located between the lower surface of the first portion and the first chamber. The portions in the closed configuration may have a snap fit with each other. For example, at least one of the chamber(s) and the finger(s) have a ridge creating the snap fit of the first and second portions.

Embodiments of the hinge connection can be a living hinge directly joining said portions. The hinge connection may be substantially parallel to the suture channel in some embodiments, and in others may be non-parallel to and offset from the suture channel. In particular examples the hinge connection is along the top surface of at least one of the first and second portions of the clamp, while in others the hinge connection is along the bottom surface of at least one of the portions. With such examples, the suture channel can include a first channel part in the first portion and a second channel part in the second portion, with the channel parts being adjacent to form the suture channel when the portions are in the closed configuration.

Embodiments of clamps can include a suture channel having a plurality of linearly-aligned holes, each of which holes communicate with at least one of the chamber(s). A particular example of chamber(s) includes a floor surface, a ceiling surface, and a side wall surface that is part-cylindrical, each of the floor surface and ceiling surface having respective holes that form part of the suture channel. A particular example of finger(s) is sized and configured to snap into the chamber(s) so that at least a part of the respective finger(s) is interposed between the respective holes in the floor surface and ceiling surface.

Methods relating to such suture clamps are also disclosed. For example, a method may include inserting a suture anchor into a patient so that a portion of the suture of the suture anchor extends out of the patient. A suture clamp having first and second portions with a hinge connection is moved along the suture, with the suture extending through a suture channel in the clamp and being maintained in tension, so that the clamp is against the skin of the patient. At least one of the first and second portions at the hinge connection are pivoted so that the first and second portions engage each other and maintain that engagement in a closed configuration. In that closed configuration, the suture of the suture anchor is maintained in tension exclusively by force exerted on the suture by the suture clamp in the closed configuration. Other examples feature the first portion of the suture clamp including at least one chamber and the second portion of the suture clamp having at least one finger. The pivoting can result in the at least one finger entering the at least one chamber so that the at least one finger is non-parallel to the suture channel and extends through the suture channel. The suture clamp can include a lower part for contacting the skin of the patient, and a method can include assembling the suture clamp by inserting a portion of the lower part into at least one of the first and second portions of the clamp.

These and other embodiments and features will be observed in the text and drawings herein.

DESCRIPTION OF THE ILLUSTRATED EMBODIMENTS

For the purposes of promoting an understanding of the principles of the disclosure, reference will now be made to the embodiments illustrated in the drawings and specific language will be used to describe the same. It will nevertheless be understood that no limitation of the scope of the claims is thereby intended, and alterations and modifications in the illustrated device, and further applications of the principles of the disclosure as illustrated therein are herein contemplated as would normally occur to one skilled in the art to which the disclosure relates.

Figure 1:
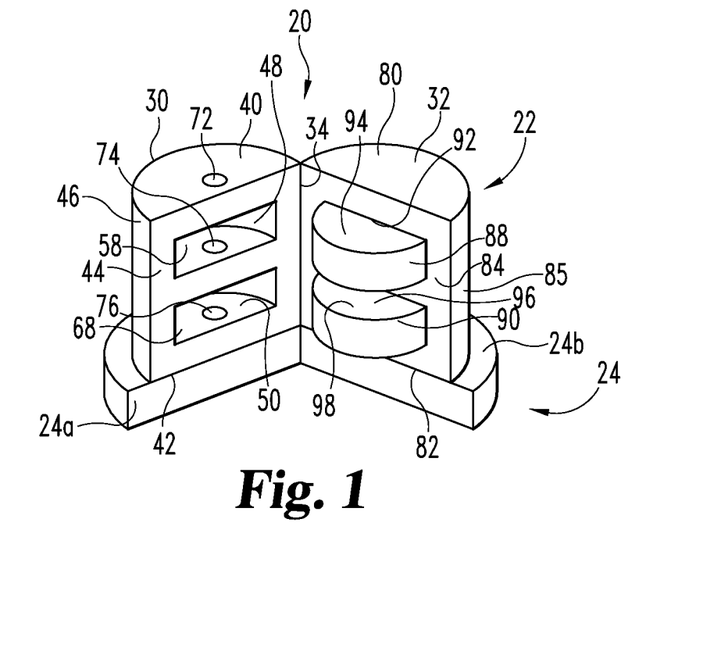
FIG. 1 is a perspective view of an embodiment of a suture clamp in an open configuration.

Referring now generally to FIG. 1, there is shown an embodiment of a suture clamp 20. Clamp 20 includes an upper part 22 and a lower part 24 that are connected together. As will be explained further below, parts 22 and 24 may be separately made and later joined together, or may be molded or otherwise fashioned together substantially at the same time. As used in this context herein, "upper" and "lower" refer to general orientation relative to a patient's skin, with "lower" indicating closer to or against the skin and "upper" indicating further from the skin.

Figure 2:
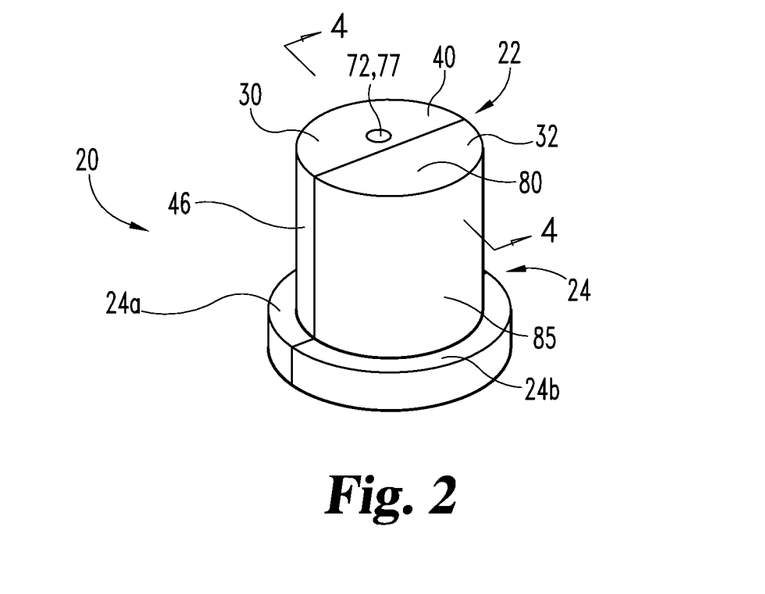
FIG. 2 is a perspective view of the embodiment of FIG. 1 in a closed configuration.

Part 22 includes first and second portions 30, 32 joined by a living hinge 34 in embodiments such as that in FIG. 1. As a particular example, each of portions 30, 32 is generally half of a circular cylinder, for ease of manufacture and handling, and to provide a similar strength or sturdiness in each portion 30, 32. In that example, when portions 30 and 32 are placed together in a closed configuration (e.g. FIG. 2) part 22 is in the general shape of a circular cylinder, and when they are pivoted away from each other around hinge 34 half-cylindrical portions 30 and 32 are joined in the hinge 34 but otherwise separated (e.g. FIG. 1). It will be understood that part 22 and/or portions 30, 32 may be of other configuration, such as a rectangular solid or oval cylinder for part 22, or portions 30, 32 may be of unequal size or dissimilar shape or configuration. As will be discussed further, portions 30 and 32 fit together with a snap fit in the illustrated embodiment in the closed configuration.

First portion 30 of part 22 has an upper surface 40 and a lower surface or edge 42. Between surfaces 40 and 42 is an interior-facing surface 44, which is planar in the illustrated embodiment. An exterior wall 46 is part-cylindrical in this embodiment, as is indicated above. Portion 30 includes at least one chamber, and in the illustrated embodiment has two chambers 48 and 50. Chambers 48 and 50 are vertically and/or axially placed relative to each other in this embodiment, with chamber 48 being above or closer to upper surface 40 and chamber 50 being below or closer to lower surface or edge 42. Chamber 48 is bounded by a floor surface 52, a ceiling surface 54, and a side wall surface 56 (FIG. 3) and having an opening 58 through surface 44. In the illustrated embodiment, surfaces 52 and 54 have one or more small lips, ridges or protrusions 60 (FIG. 4) extending from one or both of surfaces 52 and 54 to permit a snap-fit retention of second portion 32, as will be discussed further below. Surfaces 52, 54 may be substantially planar in part or in general. Side wall surface 56 is parallel to exterior wall 46 in this embodiment, e.g. part-cylindrical, so that chamber 48 has the general shape of a part of a disc. In embodiments in which portion 30 forms half of a cylinder, or in which it is half of part 22, wall surface 56 extends around about 180 degrees, and chamber 48 is of the shape of half a disc. Opening 58 is generally rectangular in the illustrated embodiment.

Figure 3:
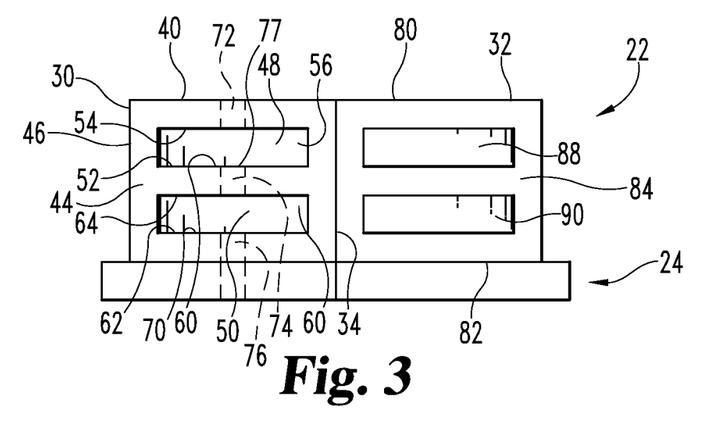
FIG. 3 is a side elevational view of the embodiment of FIG. 1 in an open configuration.
Figure 4:
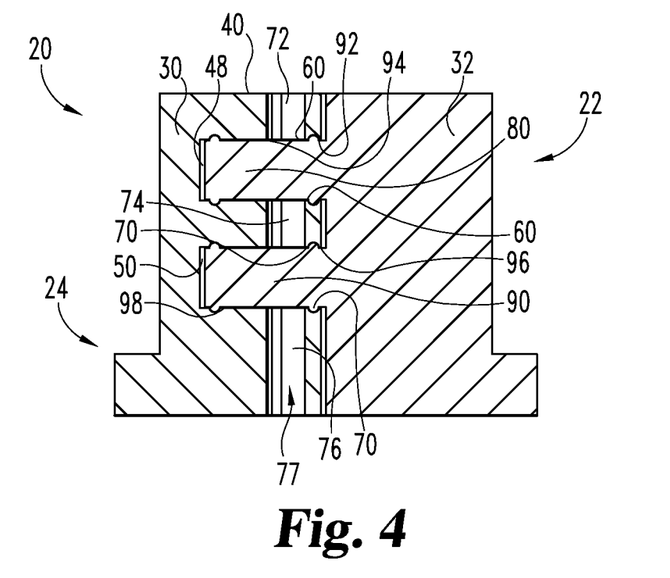
FIG. 4 is a cross-sectional view taken along the lines 4-4 in FIG. 2 and viewed in the direction of the arrows.

Chamber 50 is configured substantially similarly or identically to chamber 48 in the illustrated embodiment. Accordingly, chamber 50 is bounded by a floor surface 62, a ceiling surface 64 and a side wall surface 66, with an opening 68, which are configured similarly or identically to surfaces 52, 54 and 56 opening 58 noted above. Protrusion(s) or ridge(s) 70 extend from one or both of surfaces 62 and 64 at or adjacent to opening 68, as with ridge 60. In the illustrated embodiment, chambers 48 and 50 have substantially the same dimensions and orientation, but are vertically displaced from each other. That is, as seen in FIGS. 1, 3 and 4, chambers 48 and 50 have the same lateral extent and inside height in this embodiment, but chamber 48 is above or at a position more distal from part 24. Other embodiments that include multiple chambers in portion 30 may have the chambers similarly vertically oriented, or they may be horizontally, diagonally or non-linearly oriented. As will be explained further below, linear orientation of multiple chambers (e.g. 48 and 50) tends to make clamp 20 easier to use.

Portion 30 further includes a series of holes for accommodating a suture, so that the suture is threaded through clamp 20 and clamp 20 can be moved along the suture. Hole 72 extends between upper surface 40 and ceiling surface 54, so that chamber 48 communicates through hole 72 to the exterior of clamp 20. Hole 74 extends between floor surface 52 of chamber 48 and ceiling surface 64 of chamber 50, so that chambers 48 and 50 communicate with each other through hole 74. Hole 76 extends through floor surface 62 of chamber 50 through lower edge 42 of portion 30 and through part 24 connected to portion 30. In the illustrated embodiment, holes 72, 74, 76 are coaxial, forming parts of a linear suture channel 77 that extends from the exterior of portion 30 through each of chambers 48 and 50 to the lower end of portion 30 and through part 24. As will be explained further below, the suture threads through each of holes 72, 74 and 76 so that a portion of the suture is within chambers 48 and 50.

Second portion 32 of part 22 has an upper surface 80 and a lower surface or edge 82. Between surfaces 80 and 82 is an interior-facing surface 84, which is complementary to interior surface 44 of portion 30, e.g. planar in the illustrated embodiment. In some embodiments of the closed configuration of clamp 20 (e.g. FIG. 2), surfaces 44 and 84 face each other in adjoining contact. An exterior wall 85 is complementary to wall 46 of portion 30. Portion 32 includes at least one finger or protrusion that is adapted to be at least partially inserted into and held within a chamber of portion 30 in a snap-fit. The illustrated embodiment of portion 32 includes a first finger 88 that fits into chamber 48 and a second finger 90 that fits into chamber 50. Finger 88 includes a base portion 92 extending from surface 84 and an end or head portion 94. Head portion 94 has a dimension slightly larger than the dimension of chamber 48 at lip or ridge 60, and base portion 92 has a dimension approximately the same as or slightly smaller than the dimension of chamber 48 at ridge 60. In some embodiments, a groove may be found in base portion 92 or between base portion 92 and head portion 94 to accommodate ridge(s) 60. In the illustrated embodiments, finger 90 is substantially identical to finger 88, with a base 96 and head portion 98 configured in the same or substantially similar form. As chambers 48 and 50 are semi-cylindrical in the embodiment of FIG. 1, exemplary fingers 88 and 90 have a semi-cylindrical form of similar size and configuration to chambers 48 and 50. The exterior of portion 32 in this embodiment is complementary to the exterior of portion 30, so that when clamp 20 is in a closed condition the exterior is substantially continuous, e.g. in a cylindrical configuration in the embodiment shown in FIG. 2.

Part 24 in the illustrated embodiment is disc-shaped, having a diameter substantially larger than that of part 22 and a height substantially less than that of part 22. Part 24a is a half- or part-disc attached to portion 30 and part 24b is a half- or part-disc attached to portion 32, so each of parts 24a and 24b travel/move with its respective portion 30, 32. With clamp 20 in a closed configuration, with portions 30 and 32 of part 22 engaged (e.g. respective interior surfaces 44, 84 facing each other and in contact with or adjacent each other), parts 24a and 24b meet each other to form a whole disc of part 24, just as surfaces 46, 85 join or are adjacent to form a cylinder in this embodiment. Because part 24 is intended to contact or seat on a patient's skin (e.g. his or her abdomen), part 24 is made of a soft material to minimize discomfort to or negative reaction from the patient's skin. For example, part 24 may be made from an elastomeric material such as silicone or rubber. In particular embodiments, part 24 is made separately from part 22, and parts 22 and 24 are assembled at a later time, as by mechanical connection, gluing or other adhesive attachment, welding or other joining techniques as further described below. It will also be understood that the entirety of clamp 20 may be made of a single piece of a single material, such as the elastomeric material described above with respect to part 24.

The use of clamp 20 will now be described in the context of the placement of a gastric suture anchor to lift or pull the stomach against the abdomen wall. It will be understood that clamp 20 may be used in other situations to maintain tension on a suture or similar medical item. In some embodiments clamp 20 is provided to the surgeon or other user with a suture already extending through holes 72, 74, 76, e.g. at or toward a proximal end of the suture, with clamp 20 in an open or disengaged configuration. The distal or anchor end can be inserted into the patient without clamp 20 being involved or getting in the way of such placement.

Once the anchor is percutaneously placed within the stomach and the physician or other medical professional has moved the stomach wall next to the abdominal wall so that the stomach and abdomen are in contact or adjacent, or otherwise positioned in a position desired to be maintained, the suture portion 100 of the anchor extends from the stomach through the abdominal wall W and skin S of the patient. Tension on suture 100 maintains the stomach wall and abdomen in their relative positions. With suture 100 under tension, clamp 20 in the open or disengaged condition is advanced along suture 100, with portions of suture 100 traveling through holes 72, 74, 76 and chambers 48 and 50. Clamp 20 is advanced until part 24 is against the patient's skin. As noted above, part 24 is elastomeric in particular embodiments. In such cases, part 24 may be advanced until it at least partially conforms to the skin and/or is compressed between the skin and part 22.

When clamp 20 engages the skin, suture 100 is under tension and extends through channel 77 (e.g. holes 72, 74, 76) and chambers 48, 50 of clamp 20. The user then pivots portion 32 around hinge 34 toward portion 30, bracing or otherwise maintaining portion 30 in place so as to minimize or eliminate displacement or other disturbance of taut suture 100. In the illustrated embodiment, portion 32 is pivoted around living hinge 34 so that fingers 88 and 90 are adjacent or slightly within their respective chambers 48, 50 (or their openings 58, 68). Part 32 is further pressed against the braced portion 30 so that fingers 88, 90 are forced into chambers 48, 50. Head portions 92, 96 of fingers 88, 90 are forced past lips 60, 70 of chambers 48, 50 to snap into chambers 48, 50. Fingers 88, 90 are held within chambers 48, 50.

As fingers 88, 90 enter and snap into chambers 48, 50, head portions 92 engage and push tensioned suture 100 further into chambers 48, 50 (e.g. toward side wall surfaces 56, 86). In embodiments in which the tolerance or distance between head portions 92 and side wall surfaces 56, 86 are approximately the same as or smaller than the diameter of suture 100, suture 100 may be pinched or pressed between head portions 92 and surfaces 56, 86. An interference fit is created in such cases between suture 100 and portions 92 and/or surfaces 56, 86, with one or more of suture 100, portions 92 and surfaces 56, 86 being compressed or deformed into a complementary fit. In the illustrated embodiments, force is applied to suture 100 from the side, not along the axis of the suture, so as not to loosen tension or place too much additional tension on the suture. Suture 100 is pulled tighter as it is pushed from the side by fingers 88, 90, increasing or maintaining the tension forcing anchor an stomach against the abdomen, and pulling suture 100 toward or into chambers 48, 50 from upper and lower directions.

For example, a middle portion of suture 100 (e.g. that part of suture 100 in hole 74 between chambers 48, 50) may remain in place as fingers 88, 90 enter the respective chambers 48, 50. The fingers 88, 90 push respective portions of suture 100 on either side of that middle with equivalent force, so that there is little or no resultant force to move the section of suture 100 between fingers 88, 90 one way or the other in hole 74. With that middle section of suture 100 anchored in hole 74, upper finger 88 pushes suture 100 so that additional suture 100 enters hole 72 and chamber 48, with the additional amount of suture 100 extending around head 92 of finger 88. Similarly, lower finger 90 pushes suture 100 so that additional suture 100 enters hole 76 and chamber 50, with the additional amount of suture 100 extending around head 92 of finger 90. Accordingly, the middle portion of suture 100 within clamp 20 and/or the substance of part 30 around hole 74 acts as a stationary anchor-point, with fingers 88, 90 pulling additional suture 100 into clamp 20 to maintain or increase tension on suture 100 and its hold on the anchoring portion within the body. Addition of tension to suture 100 is thus spread between upper and lower part of the suture, giving less chance of breaking the suture between the clamp and the skin or within the skin, or of damaging tissue through which the suture extends.

Figure 5A:
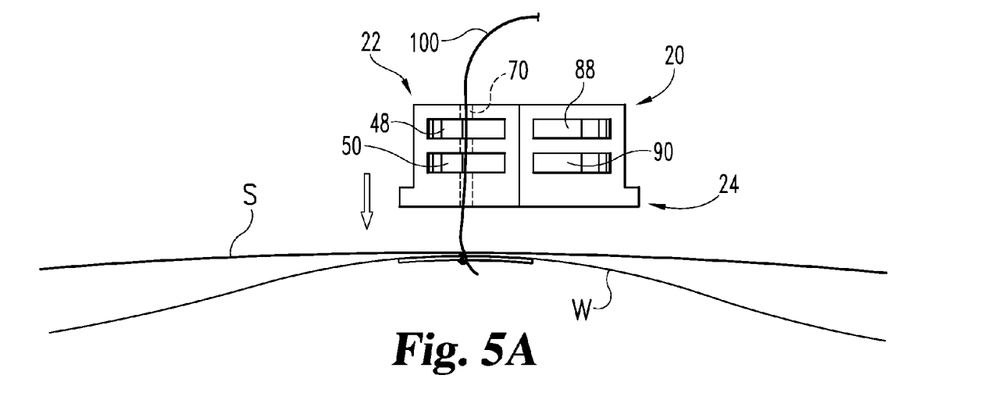
FIGS. 5A-5C are representations of aspects of use of the embodiment of FIG. 1.
Figure 5B:
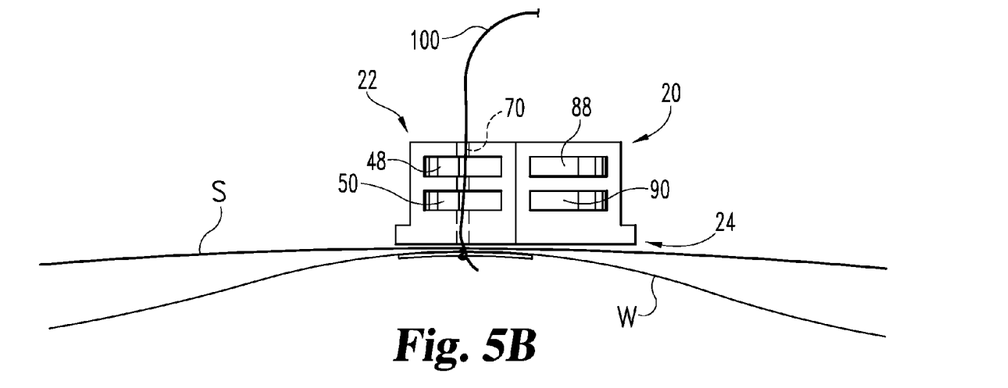
Figure 5C:
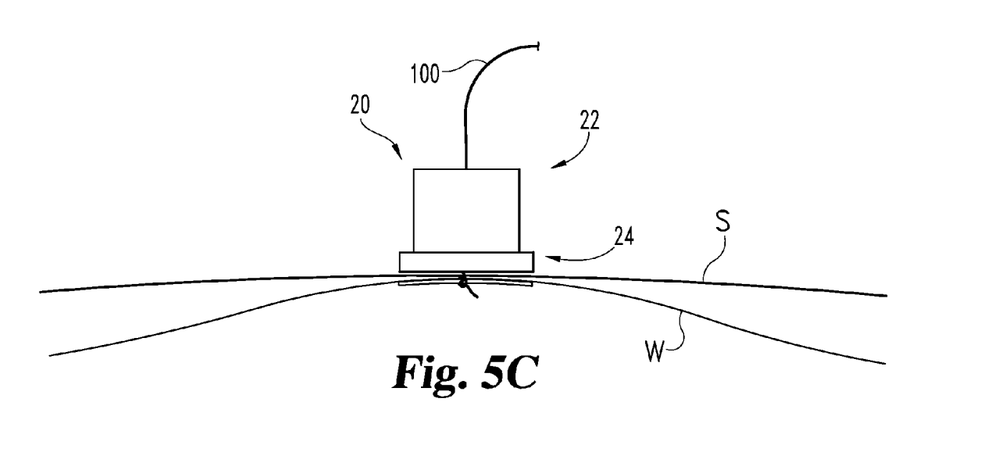

With portions 30 and 32 snapped together into the closed configuration (e.g. FIGS. 2, 5C), suture 100 is firmly locked in clamp 20 with tension on the anchor (i.e. the force holding tissues W and S together) maintained or increased over the tension level initially applied by the user. In particular embodiments suture 100 is held at multiple locations by fingers 88, 90 in chambers 48, 50. The portion of suture 100 extending from hole 72 of closed or locked clamp 20 can be cut off as excess.

When it is desired to release the tension on suture 100, e.g. when the need for the anchor to hold the stomach against the abdominal wall ends, clamp 20 can be removed from suture 100, and suture 100 may be cut close to the skin, with the portion inside the body left to be resorbed. For example, clamp 20 may be unsnapped by pulling or prying one or both of portions 30, 32 away from the other so that fingers 88, 90 exit from chambers 48, 50 or at least release the hold on suture 100. To assist in separating portions 30, 32, a groove or slot can be included in one or both portions 30, 32 to allow insertion of a flat blade, tool, or other prying device. As an example, the embodiment of FIG. 1 could include a slot or indentation between portions 30 and 32 permitting insertion of a prying device. Alternatively, if portions 30, 32 are made of polymeric or other substance that is easily shearable, clamp 20 can be cut to assist in removal. As one example, living hinge 34 can be cut part or all of the way from top to bottom to help separate portions 30, 32. As another example, clamp 20 may be cut between its upper and lower ends, e.g. between fingers 88 and 90 or along finger 90, to reduce or eliminate the holding ability of the joined fingers 88, 90 and chambers 48, 50. With clamp 20 open or suture 100 released, clamp 20 can be removed along suture 100, with suture 100 passing through at least a portion of channel 77 (e.g. through one or more of holes 72, 74, 76). Once clamp 20 is off of suture 100, a new clamp 20 or other device can be placed or used to hold suture 100. If holding of suture 100 is no longer needed, then suture 100 can be cut close to the skin, and the amount of suture 100 below the skin is allowed to resorb into the body.

Figure 6:
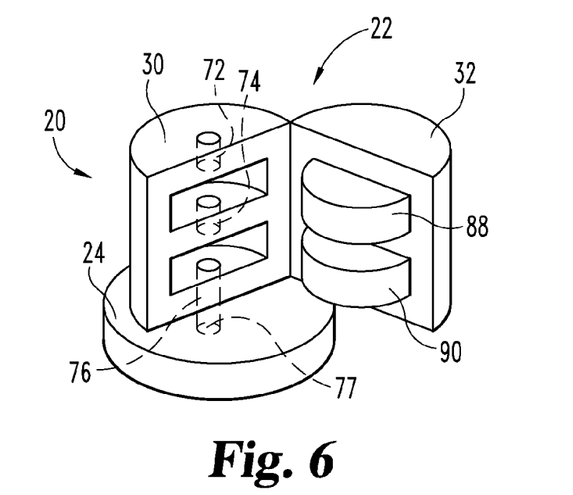
FIG. 6 is a perspective view of an embodiment of a suture clamp in an open configuration.

As indicated above, some embodiments of clamp 20 include a part 24 split in the same fashion as part 22, so that as part 22 is closed (by pushing one or both of portions 30, 32 toward each other), the parts 24a and 24b of part 24 pivot toward each other to close as well. In other embodiments, only one portion of part 22 (e.g. portion 30) is attached to a full-disc part 24, as indicated in FIG. 6. The other portion (e.g. portion 32 in this example) is not directly attached to part 24, and is rotatable about hinge 34 with respect to part 24. A single, one-part disc 24 is thus provided, with part 32 pivotable with respect to it.

The embodiments of clamps 20 shown and described with respect to FIGS. 1-6 permit holding or maintaining part 30 stationary, with suture 100 through it, and moving part 32 to close clamp 20 is preferable. Such constructions may be preferred where motion of suture 100 while applying tension may be difficult or undesirable. Doing so may result in an inadvertent loss of tension, or in irritation of or damage to tissue by a tensioned suture as part 30 is moved. In certain embodiments, however, the user can hold part 32 and move part 30 in closing clamp 20 to hold a suture, especially if additional pulling or tension on the suture is desired. For example, reversing the configuration of FIG. 6, with portion 32 anchored to part 24 and portion 32 pivotable with respect to part 24, allows pivoting of portion 30 against portion 32 to close clamp 20.

The examples of FIGS. 1-4 demonstrate hinge 34 parallel to channel 77 for suture 100. In these embodiments, the entireties of the side edges of portions 30, 32, i.e. from the bottom to the top of each of portions 30, 32, are joined in hinge 34. It is believed that having the entire edges joined in a living hinge provides substantial durability, and it also ensures that portions 30, 32 rotate directly together around a common axis. Such an attachment leaves little or no risk of portions 30, 32 being improperly oriented when it is time to snap them together.

Figure 7:
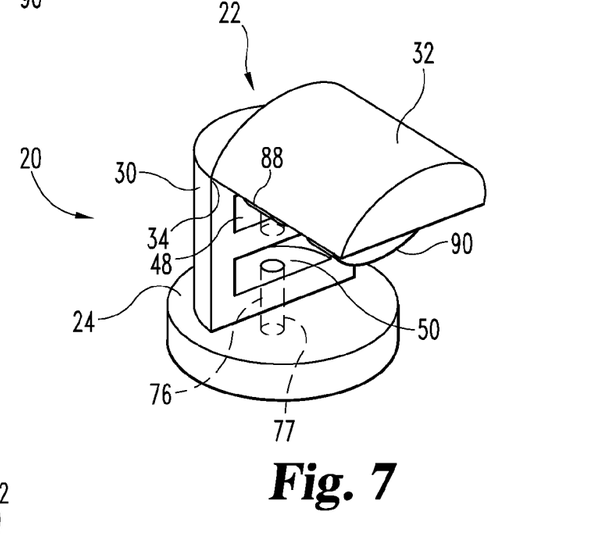
FIG. 7 is a perspective view of an embodiment of a suture clamp in an open configuration.

Other embodiments may have a joining living hinge 34 between portions 30, 32 in other positions or angles relative to channel 77 (e.g. holes 72, 74, 76). FIG. 7 shows an embodiment in which hinge 34 is perpendicular and offset from the axis of holes 72, 74, 76 at the top of clamp 20 (e.g. at or near one or both of surfaces 40, 80). In this embodiment, portion 30 remains stationary against the skin with suture 100 through it, and portion 32 is pivotable around hinge 34 with respect to portion 30 with a downward (i.e. toward part 24) pivoting motion used to snap portions 30 and 32 together. As indicated above, when portion 32 pivots toward portion 30, fingers 88, 90 enter and snap into chambers 48, 50 to add tension to suture 100 and hold it within clamp 20.

Figure 8:
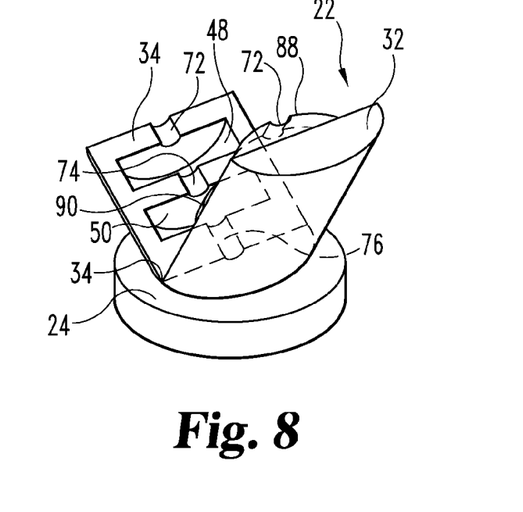
FIG. 8 is a perspective view of an embodiment of a suture clamp in an open configuration.
Figure 9:
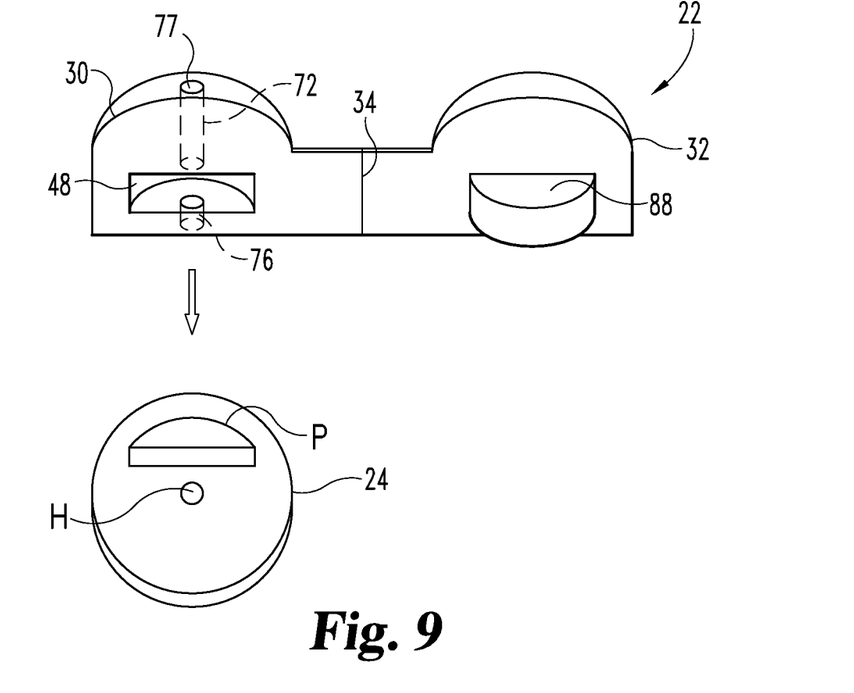
FIG. 9 is a perspective view of parts of an embodiment of a suture clamp in an open configuration.
Figure 10:
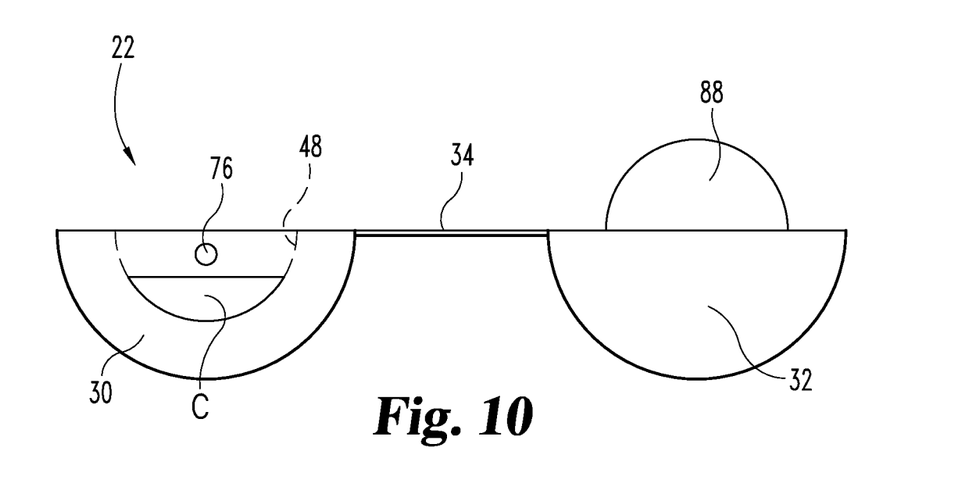
FIG. 10 is a bottom view of a portion of the embodiment as shown in FIG. 9.
Figure 11A:
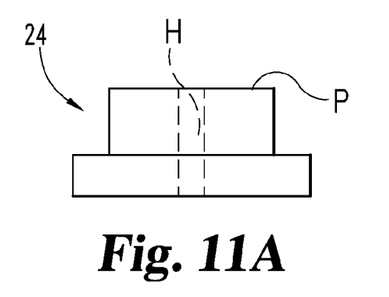
FIGS. 11A-11F are representations of embodiments of parts usable in the suture clamps illustrated and described herein.
Figure 11B:
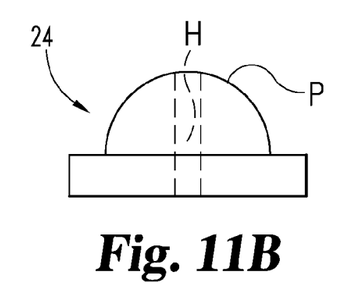
Figure 11C:
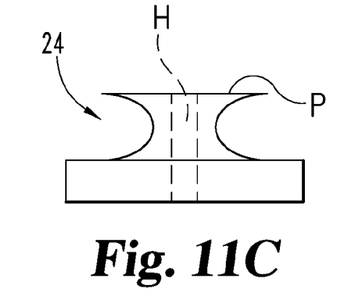
Figure 11D:
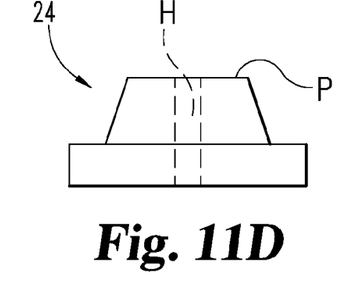
Figure 11E:
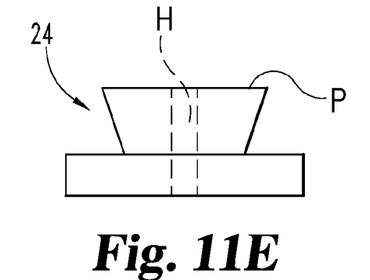
Figure 11F:
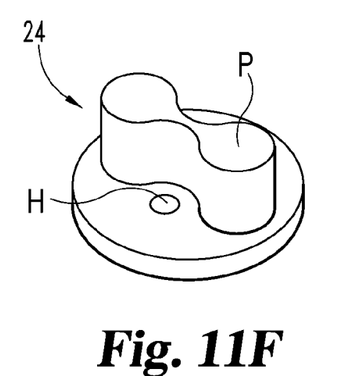

In the embodiment of FIG. 8, both portions 30 and 32 are pivotable about living hinge(s) with respect to part 24. A channel 77 for suture 100 has a portion through part 24 and portions 72, 74, 76 in the walls of portions 30, 32. The illustrated embodiment shows semi-cylindrical portions 72, 74, 76 of channel 77 in each of portions 30, 32, so that a full-cylindrical channel 77 is formed with portions 30, 32 are forced together. As with the above embodiments, with suture 100 in tension, portions 30 and 32 are squeezed together so that fingers 88, 90 push suture 100 into chambers 48, 50. Suture 100 is not only held within chambers 48, 50, but is further tensioned, as noted above.

Part 22 may be attached to part 24 in a number of ways. In the embodiment of FIG. 1, parts 22 and 24 may be fabricated together, with living hinge 34. In other embodiments, separate parts 30 and 32 may be fabricated and joined together via snapping fit, interference fit, adhesive(s), welding and/or via other techniques. In such cases, examples of which are shown in FIGS. 9-11F, a part 22 has a cavity C and a part 24 has a protrusion P that fits into cavity C. Such a fit may be a snapping, press or interference fit, or maintained within cavity C by adhesive, welding, or other connection. In particular examples, cavity C is in a bottom surface of portion 30 of a part 22, so that when part 22 is joined to part 24 by insertion of protrusion P into cavity C, portion 32 of part 22 is pivotable around hinge 34 relative to the joined combination of part 24 and portion 30. FIG. 7 indicates an example of a clamp 20 with separately-made parts 22 and 24. Part 22 includes a portion 30 with a single chamber 48 and holes 72 and 76 forming at least part of a channel 77 as discussed above, and a cavity C (part-circular or part-cylindrical in the illustrated embodiment) is in the bottom of portion 30. Portion 32 includes one finger 88 configured to securely fit within chamber 48, as discussed above. Part 24, in the illustrated example, has a disc-shaped base and part-circular or part-cylindrical protrusion P shaped and configured to fit and/or be held within cavity C. An open hole H through protrusion P or other portion of part 24 communicates with hole 76 and so forms a part of channel 77. The user can assemble parts 22 and 24 in preparation for or during use, as described generally below.

FIGS. 8A-8G demonstrated examples of such parts 24 that may be separately fabricated and attached to part(s) 22 that are similarly or compatibly configured. In each case, part 24 includes a substantially-flat disc portion, and an upwardly extending mating portion or protrusion P. In FIG. 8A, protrusion P is a substantially cylindrical or disc-like extension. In FIG. 8B, protrusion P is part of a sphere, e.g. a hemisphere. FIG. 8C shows protrusion P as a disc or cylinder with a rounded groove G. In FIGS. 8D and 8E, protrusion P is a frustum of a cone, with the broad end against the disc portion in FIG. 8D, and the narrow end against the disc portion in FIG. 8E. FIG. 8F shows a protrusion P in the shape of an oblong cylinder with side indentations. It will be understood that other regular and irregular shapes for protrusion P may be considered for use, with the above examples being those considered likely to be particularly useful. Each of the protrusions P in these examples may include a lip or flange to interact with a part 22 that has a similarly sized and/or configured cavity C, to make a firm snap, interference or other connection. Adhesive may be placed on part or all of such protrusions P and/or within compatible cavities C of a part 22 to firmly attach parts 22 and 24 together.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to a specific embodiment may be used or incorporated into other embodiments of the structures and methods disclosed.

What is claimed is:

1. A suture clamp, comprising:
   first and second portions with a hinge connection joining them, said first portion having an upper surface, a lower surface, at least one chamber between said upper and lower surfaces, and a suture channel, said suture channel including a first opening through said upper surface and a second opening through said lower surface, said suture channel passing through said at least one chamber;
   wherein said second portion has an upper surface, a lower surface, and at least one finger, each of said at least one finger being sized and configured to fit within a respective one of said at least one chamber; and
   a lower disc part attached to the lower surface of at least one of said first and second portions,
   wherein said portions are pivotable about said hinge connection between an open configuration in which said at least one finger is not within said at least one chamber and a closed configuration in which said at least one finger is at least partially within said at least one chamber so that said suture channel intersects said at least one finger,
   so that in said open configuration a suture extending through said suture channel can be linear as it passes through said at least one chamber, and in said closed configuration the suture is non-linear within said at least one chamber and contacts at least a portion of said at least one finger within said at least one chamber, and
   wherein said lower disc part is elastomeric and has a diameter larger than a diameter of said portions in said closed configuration.

2. The suture clamp of claim 1, wherein said lower disc part is monolithic with one of said portions.

3. The suture clamp of claim 1, wherein said lower disc part includes a protrusion, and at least one of said portions includes a cavity for accommodating said protrusion, and wherein said portions and said lower disc part are assembled by inserting said protrusion into said cavity.

4. The suture clamp of claim 1, wherein said hinge connection is a living hinge directly joining said portions.

5. The suture clamp of claim 1, wherein said first portion includes first and second chambers separated by a partition, said partition forming a surface of said first chamber and a surface of said second chamber, and wherein said suture channel includes an opening between said first and second chambers through said partition, and wherein said second portion includes first and second fingers sized and configured to snap fit within said first and second chambers, respectively.

6. The suture clamp of claim 5, wherein said first chamber is located between said upper surface of said first portion and said second chamber, and said second chamber is located between said lower surface of said first portion and said first chamber.

7. The suture clamp of claim 1, wherein in said closed configuration said first and second portions have a snap fit with each other.

8. The suture clamp of claim 7, wherein at least one of said chamber and said finger have a ridge creating said snap fit of said first and second portions.

9. The suture clamp of claim 1, wherein said hinge connection is substantially parallel to said suture channel.

10. The suture clamp of claim 1, wherein said hinge connection is non-parallel to said suture channel and offset from said suture channel.

11. The suture clamp of claim 10, wherein said hinge connection is along the top surface of at least one of said portions.

12. The suture clamp of claim 10, wherein said hinge connection is along the bottom surface of at least one of said portions.

13. The suture clamp of claim 12, wherein said suture channel includes a first channel part in said first portion and a second channel part in said second portion, said channel parts being adjacent to form said suture channel in said closed configuration.

14. The suture clamp of claim 1, wherein said suture channel includes a plurality of linearly-aligned holes, each of said linearly-aligned holes communicating with at least one of said at least one chamber.

15. The suture clamp of claim 1, wherein said at least one chamber includes a floor surface, a ceiling surface, and a side wall surface that is part-cylindrical, each of said floor surface and said ceiling surface having respective holes that form part of said suture channel, and wherein said at least one finger is sized and configured to snap into said at least one chamber so that at least a part of said at least one finger is interposed between said holes in said floor surface and said ceiling surface.

* * * * *